(12) United States Patent
Pan et al.

(10) Patent No.: US 10,987,394 B2
(45) Date of Patent: Apr. 27, 2021

(54) **METHOD FOR PREPARING AN EXTRACT OF *CHRYSANTHEMUM MORIFOLIUM* WITH AN EFFECT OF TREATING SKIN DISEASES, EXTRACT OF *CHRYSANTHEMUM MORIFOLIUM* WITH AN EFFECT OF TREATING SKIN DISEASES AND PHARMACEUTICAL COMPOSITION CONTAINING THE EXTRACT**

(71) Applicant: Industrial Technology Research Institute, Hsinchu (TW)

(72) Inventors: I-Horng Pan, Zhubei (TW); Hsin-Jan Yao, Yunlin County (TW); Chu-Hsun Lu, Kaohsiung (TW); Shu-Fang Wen, Baoshan Township (TW); Po-Yao Hsu, Taichung (TW); Ming-Han Li, Taipei (TW); Kai-An Chuang, Taipei (TW); Chih-Hsuan Chang, Zhubei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 158 days.

(21) Appl. No.: 15/852,748

(22) Filed: Dec. 22, 2017

(65) Prior Publication Data
US 2019/0192597 A1 Jun. 27, 2019

(51) Int. Cl.
*A61K 36/28* (2006.01)
*A61K 36/00* (2006.01)
*A61K 36/287* (2006.01)
*A61K 9/00* (2006.01)
*A61P 17/06* (2006.01)
*A61P 17/04* (2006.01)

(52) U.S. Cl.
CPC .......... *A61K 36/287* (2013.01); *A61K 9/0014* (2013.01); *A61P 17/04* (2018.01); *A61P 17/06* (2018.01); *A61K 2236/19* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| 8,067,036 | B2 | 11/2011 | Kato et al. |
| 8,790,720 | B2 | 7/2014 | Richards et al. |
| 8,846,114 | B1 | 9/2014 | Makela et al. |
| 9,326,990 | B2 | 5/2016 | Morita et al. |

FOREIGN PATENT DOCUMENTS

| CN | 101036627 A | 9/2007 |
| CN | 103006938 A | 4/2013 |
| CN | 103610725 A | 3/2014 |
| CN | 104257576 A | 1/2015 |
| CN | 104274630 A | 1/2015 |
| CN | 105175376 A | 12/2015 |
| CN | 105194443 A | 12/2015 |
| CN | 105232758 A | 1/2016 |
| CN | 105769628 A | 7/2016 |
| CN | 105779165 A | 7/2016 |
| FR | 2732593 A1 * | 10/1996 |
| JP | 2007-197345 A | 8/2007 |
| JP | 2014-132894 A | 7/2014 |
| JP | 2015-63493 A | 4/2015 |
| JP | 2015212236 A * | 11/2015 |
| KR | 10-2006-0033069 A | 4/2006 |
| KR | 2006108864 A * | 10/2006 |
| KR | 10-2009-0131417 A | 12/2009 |
| KR | 2011131822 A * | 12/2011 |
| KR | 10-2014-0091376 A | 7/2014 |
| KR | 1611930 B1 * | 4/2016 |
| KR | 1738075 B1 * | 5/2017 |
| TW | 201438756 A | 10/2014 |
| WO | WO 2019/070056 A1 | 4/2019 |

OTHER PUBLICATIONS

Li et al. (Simultaneous determination of luteolin and apigenin in dog plasma by RP-HPLC, Journal of Pharmaceutical and Biomedical Analysis, 37:615 (2005), pp. 1-3, abstract) (Year: 2005).*

Chen et al. (Absorption and Excretion of Luteolin and Apigenin in Rats after Oral Administration of Chrysanthemum morifolium Extract, Journal of Agric. Food Chem. 55:273 ((2007), pp. 273-277) (Year: 2007).*

Iqbal, M., et al, "Phytochemicals as a potential source for TNF-α inhibitors," Phytochem Rev, Aug. 30, 2012, pp. 65-93.

Lin, L.C., et al, "Isolation of Luteolin and Luteolin-7-O-glucoside from Dendranthema morifolium Ramat Tzvel and Their Pharmacokinetics in Rats," Journal of Agricultural and Food Chemistry, 2015, vol. 63, pp. A-G.

Taiwanese Office Action for Appl. No. 106145261 dated Jul. 25, 2018.

Yagi, M., et al, "The Effect of Edible Purple Chrysanthemum Extract on Advanced Glycation End Products Generation in Skin: a Randomized Controlled Clinical Trial and in vitro Study," Anti-Aging Medicine, 2012, vol. 9, No. 2, pp. 61-74.

European Search Report dated Apr. 17, 2019 for corresponding EP Application No. 18195778.8.

Fu et al., Food Chemistry, "Enzyme assisted extraction of luteolin and apigenin from pigeonpea [*Cajanus cajan* (L.) *Mill*sp.] leaves", 2008, vol. 111, pp. 508-512.

(Continued)

*Primary Examiner* — Michael Barker
*Assistant Examiner* — Randall O Winston
(74) *Attorney, Agent, or Firm* — Birch, Stewart, Kolasch & Birch, LLP

(57) ABSTRACT

The present disclosure provides a method for preparing an extract of *Chrysanthemum morifolium* with an effect of treating skin diseases, including: (a) performing an extraction procedure on *Chrysanthemum morifolium* with an extraction solvent to obtain an extract solution; and (b) adding at least one glycoside hydrolases to the extract solution to make an enzyme reaction occur to produce a precipitate, wherein the precipitate is the extract of *Chrysanthemum morifolium* with an effect of treating skin diseases.

36 Claims, 5 Drawing Sheets

(56) References Cited

OTHER PUBLICATIONS

Lii et al., Journal of Ethnopharmacology, "Chrysanthemum morifolium Ramat. reduces the oxidized LDL-induced expression of intercellular adhesion molecule-1 and E-selectin in human umbilical vein endothelial cells", 2010, vol. 128, pp. 213-220.

Lu et al., Pharmazie, "Evaluation of hepatic clearance and drug-drug interactions of luteolin and apigenin by using primary cultured rat hepatocytes", vol. 65, 2011, pp. 600-605.

Bouzaiene et al., "Effect of apigenin-7-glucoside, genkwanin and naringenin on tyrosinase activity and melanin synthesis in B16F10 melanoma cells" Life Sciences, 2016, vol. 144, pp. 80-85.

Byun et al., "Src kinase is a direct target of apigenin against UVB-induced skin inflammation", Carcinogenesis, 2013, vol. 34, No. 2, pp. 397-405.

Fuchs et al., "Skin anti-inflammatory activity of apigenin-7-glucoside in rats.", Arzneimittelforschung, Mar. 1993, vol. 43, No. 3, p. 370-2.

George et al., "Luteolin induces caspase-14-mediated terminal differentiation in human epidermal keratinocytes", in Vitro Cell. Dev.Biol.—Animal, 2015, vol. 51, pp. 1072-1076.

Gui et al., "Aqueous Extract of Chrysanthemum morifolium Enhances the Antimelanogenic and Antioxidative Activities of the Mixture of Soy Peptide and Collagen Peptide", Journal of Traditional and Complementary Medicine, 2014, vol. 4, No. 3, pp. 171-176.

Hou et al., "Topical apigenin improves epidermal permeability barrier homoeostasis in normal murine skin by divergent mechanisms", Experimental Dermatology, 2013, vol. 22, pp. 210-215.

Lee et al., "Inhibition of c-Kit signaling by diosmetin isolated from Chrysanthemum morifolium", Archives of Pharmacal Research, 2014, vol. 37, pp. 175-185.

Torres et al., "Small Molecules in the Treatment of Psoriasis", Drug Development Research, 2015, vol. 76, pp. 215-227.

Weng et al., "Luteolin Inhibits Human Keratinocyte Activation and Decreases NF-kB Induction That is Increased in Psoriatic Skin", PLOS One, Feb. 2014, vol. 9, Issue 2, e90739, pp. 1-8.

Xie et al., "Comparative Evaluation of Cultivars of Chrysanthemum morifolium Flowers by HPLC-DAD-ESI/MS Analysis and Antiallergic Assay", Journal of Agricultural and Food Chemistry, 2012, vol. 60, pp. 12574-12583.

Yasukawa et al., "Inhibitory effect of heliantriol C; a component of edible Chrysanthemum, on tumor promotion by 12-O-tetradecanoylphorbol-13-acetate in two-stage carcinogenesis in mouse skin", Phytomedicine, 1998, vol. 3, No. 3, pp. 215-218.

Office Action issued in Japanese Patent Application No. 2019-114564 dated Jul. 14, 2020.

* cited by examiner

US 10,987,394 B2

METHOD FOR PREPARING AN EXTRACT OF *CHRYSANTHEMUM MORIFOLIUM* WITH AN EFFECT OF TREATING SKIN DISEASES, EXTRACT OF *CHRYSANTHEMUM MORIFOLIUM* WITH AN EFFECT OF TREATING SKIN DISEASES AND PHARMACEUTICAL COMPOSITION CONTAINING THE EXTRACT

TECHNICAL FIELD

The technical field relates to a preparation method of a plant extract, and in particular it relates to a method for preparing an extract of *Chrysanthemum morifolium* with the effect of treating skin diseases, an extract of *Chrysanthemum morifolium* with the effect of treating skin diseases, and a pharmaceutical composition for treating skin diseases containing this extract.

BACKGROUND

Skin diseases are the most common disease in the world, and about one-third of the population has a pathological skin problem during his or her lifetime. In terms of health care spending, skin-related medical costs can reach as high as 25%.

Skin diseases can be divided into four major categories, namely dermatitis (such as allergic and contact), cancer (such as melanoma), immune disease (such as psoriasis), and infectious skin disease (such as bacterial, fungal, and viral infections).

Topical steroids have been used extensively in various skin conditions, especially atopic dermatitis and psoriasis, and in severe dermatitis patients, steroids are used in higher doses. Many compounds classified as steroids, such as betamethasone or prednisolone, are very effective in the treatment of inflammatory diseases. However, long-term use of these compounds may also cause skin atrophy in patients. Patients who suffer from skin atrophy during steroid treatment are generally considered as steroid responders. The influence of skin atrophy on patients already suffering from skin disease symptoms (such as psoriasis patients) is a concern. However, even with normal skin, in the case of long-term use of steroids, there can be side effects including skin damage.

Therefore, development of safe dermatological drugs that can replace steroids, especially botanicals, is an important issue.

SUMMARY

The present disclosure provides a method for preparing an extract of *Chrysanthemum morifolium* with an effect of treating skin diseases, comprising: (a) performing an extraction procedure on *Chrysanthemum morifolium* with an extraction solvent to obtain an extract solution; and (b) adding at least one glycoside hydrolases to the extract solution to make an enzyme reaction occur to produce a precipitate, wherein the precipitate is the extract of *Chrysanthemum morifolium* with an effect of treating skin diseases.

The present disclosure also provides an extract of *Chrysanthemum morifolium* with an effect of treating skin diseases, which is obtained using the aforementioned method for preparing an extract of *Chrysanthemum morifolium* with an effect of treating skin diseases.

The present disclosure also provides an extract of *Chrysanthemum morifolium* with an effect of treating skin diseases, at least comprising the following two indicator ingredients: luteolin and apigenin, wherein in the extract of *Chrysanthemum morifolium*, the content ratio of the luteolin to the apigenin is about 1:1-30.

The present disclosure further provides a pharmaceutical composition for treating skin diseases, comprising: any aforementioned extract of *Chrysanthemum morifolium* with an effect of treating skin diseases; and a pharmaceutically acceptable vehicle, carrier or salt.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

Figure 1A:
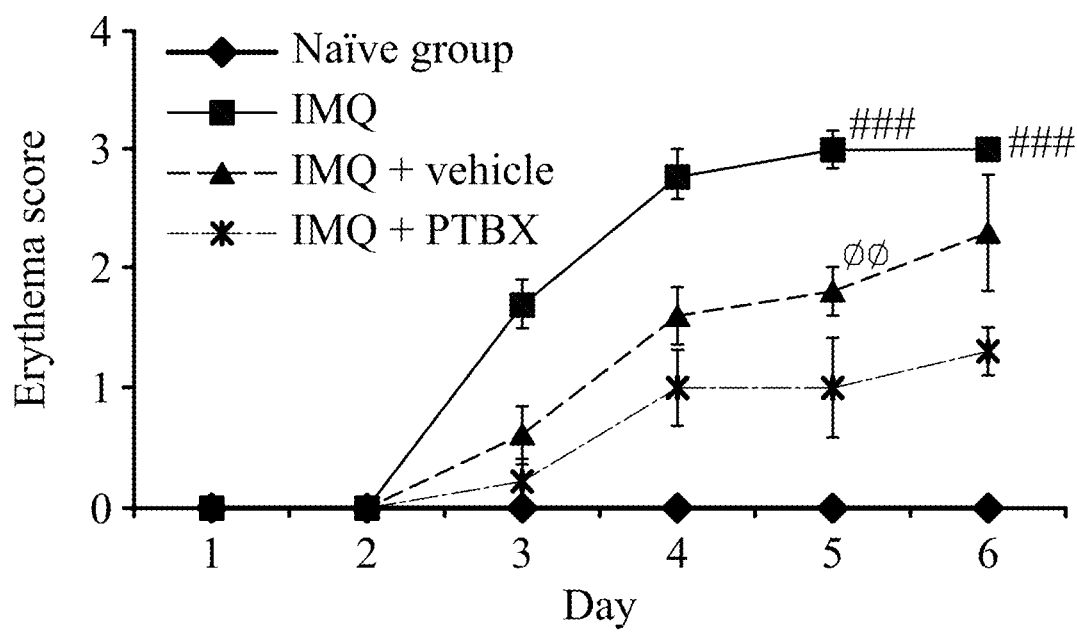
FIG. 1A shows the erythema scores of the back skin of the mice of the naïve group (no treatment is applied), the control group (50 mg imiquimod (IMQ) cream), the imiquimod (IMQ)+vehicle group (50 mg imiquimod cream+the vehicle of ointment) and the experimental group (50 mg imiquimod cream+PTBX ointment). Mean±Standard deviation. ###: $p<0.001$, as compared to the naïve group; øø: $p<0.01$, as compared to the control group. T-test.
Figure 1B:
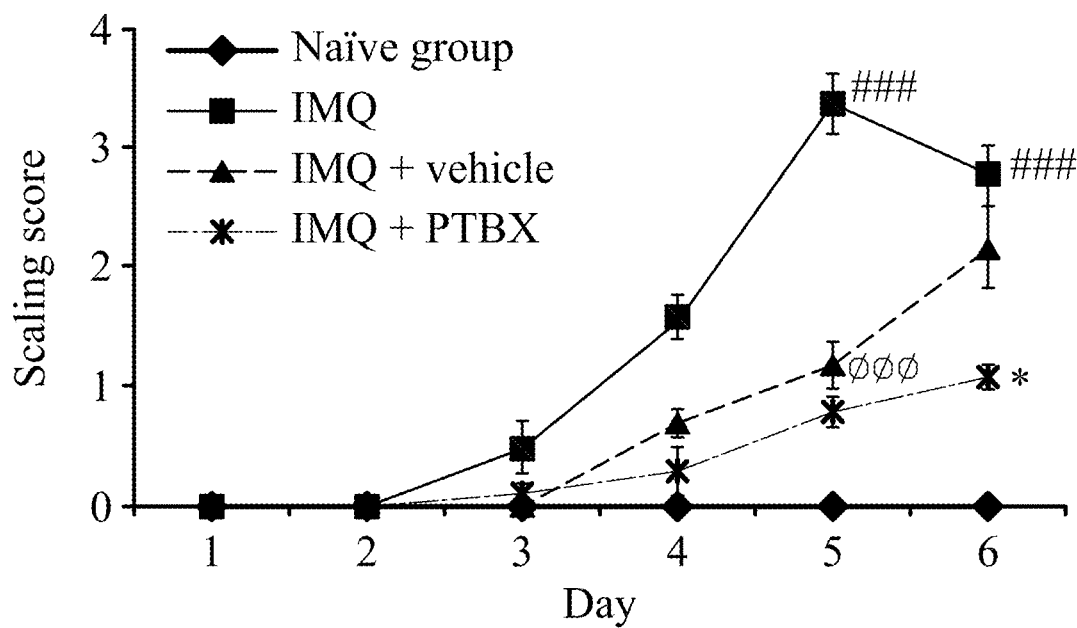
FIG. 1B shows the scaling scores of the back skin of the mice of the naïve group (no treatment is applied), the control group (50 mg imiquimod (IMQ) cream), the imiquimod (IMQ)+vehicle group (50 mg imiquimod cream+the vehicle of ointment) and the experimental group (50 mg imiquimod cream+PTBX ointment). Mean±Standard deviation. ###: $p<0.001$, as compared to the naïve group; øøø: $p<0.001$, as compared to the control group. *: $p<0.05$, as compared to the imiquimod (IMQ)+vehicle group. T-test.
Figure 1C:
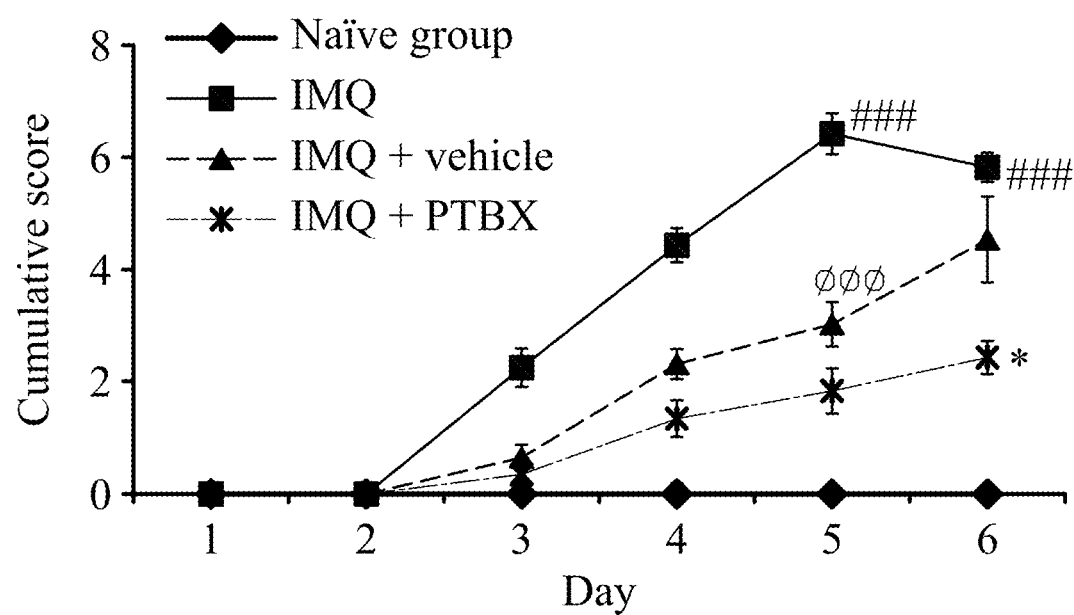
FIG. 1C shows the cumulative score of the back skin of the mice of the naïve group (no treatment is applied), the control group (50 mg imiquimod (IMQ) cream), the imiquimod (IMQ)+vehicle group (50 mg imiquimod cream+the vehicle of ointment) and the experimental group (50 mg imiquimod cream+PTBX ointment). Mean±Standard deviation. ###: $p<0.001$, as compared to the naïve group; øøø: $p<0.001$, as compared to the control group. *: $p<0.05$, as compared to the imiquimod (IMQ)+vehicle group. T-test.
Figure 1D:
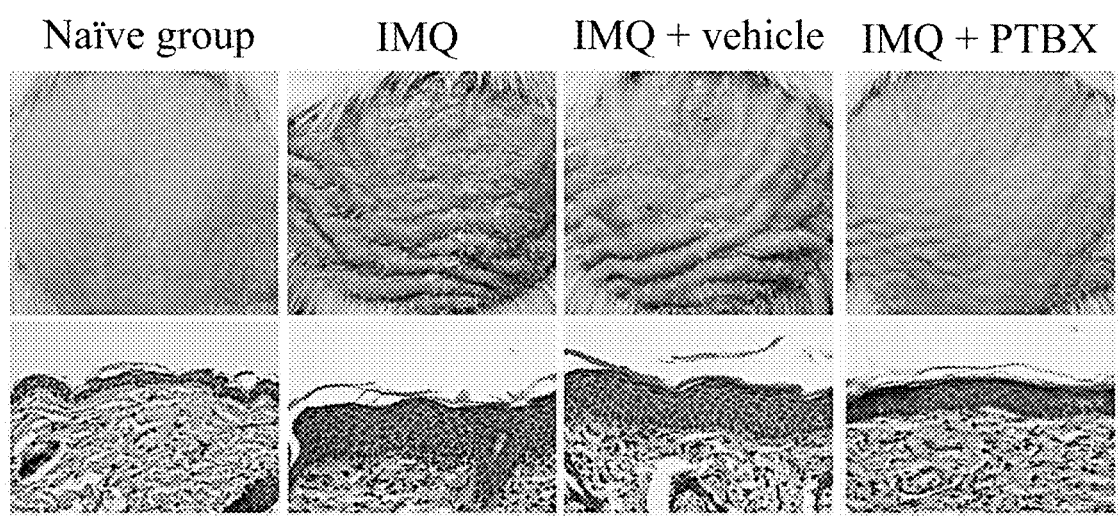
FIG. 1D shows the photographs and H&E stain results for the back skin of the mice of the naïve group (no treatment is applied), the control group (50 mg imiquimod (IMQ) cream), the imiquimod (IMQ)+vehicle group (50 mg imiquimod cream+the vehicle of ointment) and the experimental group (50 mg imiquimod cream+PTBX ointment)
Figure 1E:
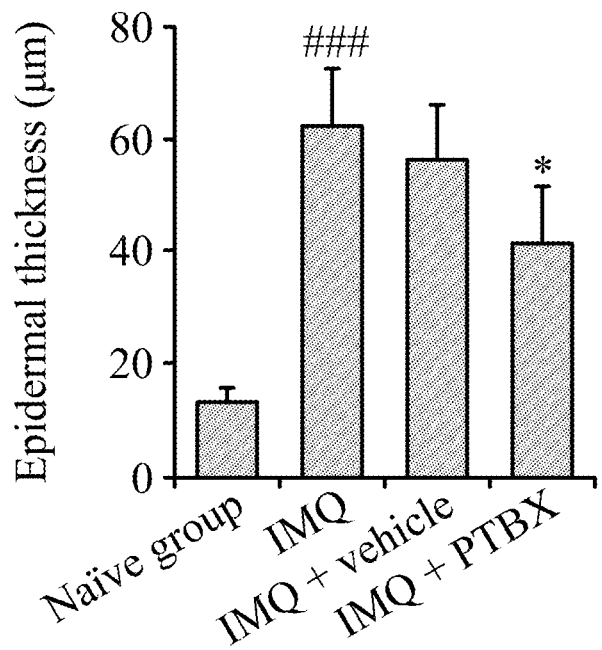
FIG. 1E shows the skin thickness of the back skin of the mice of the naïve group (no treatment is applied), the control group (50 mg imiquimod (IMQ) cream), the imiquimod (IMQ)+vehicle group (50 mg imiquimod cream+the vehicle of ointment) and the experimental group (50 mg imiquimod cream+PTBX ointment). Mean±Standard deviation. ###: $p<0.001$, as compared to the naïve group; *: $p<0.05$, as compared to the imiquimod (IMQ)+vehicle group. T-test.
Figure 1F:
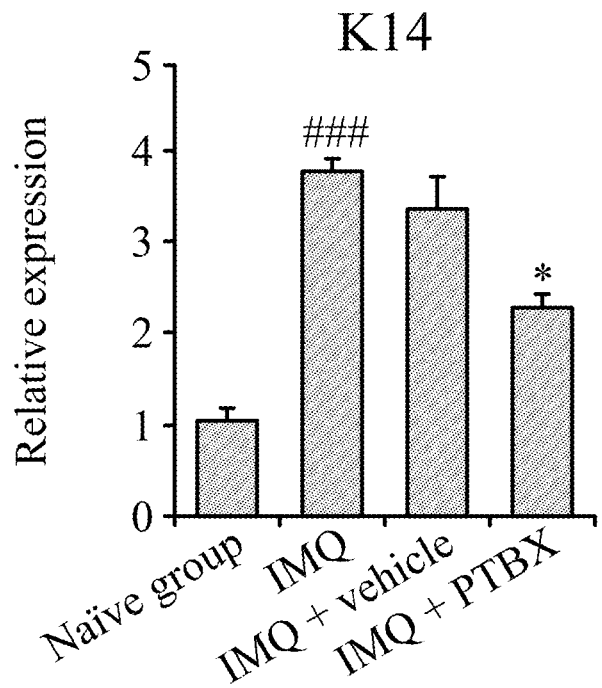
FIG. 1F shows the keratin (K14) gene expression levels of the back skin of the mice of the naïve group (no treatment is applied), the control group (50 mg imiquimod (IMQ) cream), the imiquimod (IMQ)+vehicle group (50 mg imiquimod cream+the vehicle of ointment) and the experimental group (50 mg imiquimod cream+PTBX ointment).
Figure 1G:
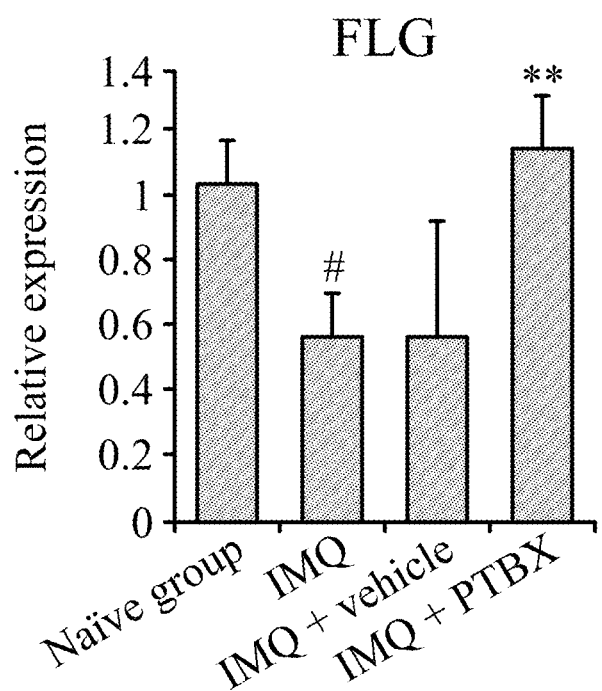

Mean±Standard deviation. ###: p<0.001, as compared to the naïve group; *: p<0.05, as compared to the imiquimod (IMQ)+vehicle group. T-test;

FIG. 1G shows the filaggrin (FLG) gene expression levels of the back skin of the mice of the naïve group (no treatment is applied), the control group (50 mg imiquimod (IMQ) cream), the imiquimod (IMQ)+vehicle group (50 mg imiquimod cream+the vehicle of ointment) and the experimental group (50 mg imiquimod cream+PTBX ointment). Mean±Standard deviation. #: p<0.05, as compared to the naïve group; **: p<0.01, as compared to the imiquimod (IMQ)+vehicle group. T-test.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure provides a method for preparing an extract of Chrysanthemum morifolium with the effect of treating skin diseases. The skin diseases described herein have no specific limitation, and may be, for example, dermatitis (such as allergic or contact), immune diseases (such as psoriasis), infectious skin diseases (such as bacterial, fungal, viral infection).

The foregoing method may comprise, but is not limited to the following steps.

First, an extraction procedure is performed on Chrysanthemum morifolium with an extraction solvent to obtain an extract solution. The foregoing extract solution may be an extract solution directly obtained from the extraction procedure, or may be a solution formed by re-dissolving a powder which is formed by further drying an extract solution directly obtained from the extraction procedure mentioned above with water or a buffer, and has no specific limitation. Moreover, examples of the buffer may comprise, but is not limited to, acetate buffer.

Moreover, examples of the extraction solvent mentioned above may include water and alcohols, but they are not limited thereto. In one embodiment, the extraction solvent may be water.

The temperature of the extraction procedure is about 70-100° C., but it is not limited thereto. In one embodiment, the temperature of the extraction procedure is about 80-95° C. Moreover, the time required for the extraction procedure may be about 1-3 hours, but it is not limited thereto. In one embodiment, the time required for the extraction procedure may be about 1-2 hours.

Next, at least one glycoside hydrolase is added to the extract solution to make an enzyme reaction occur to produce a precipitate, and the obtained precipitate is the extract of Chrysanthemum morifolium with the effect of treating skin diseases.

The weight ratio of the foregoing glycoside hydrolase to the foregoing Chrysanthemum morifolium may be about 1:200-10000, such as 1:3000-8000, 1:1500-4000, 1:750-2000, 1:300-800, but it is not limited thereto. In one embodiment, the weight ratio of the foregoing glycoside hydrolase to the foregoing Chrysanthemum morifolium may be about 1:3000-8000. In another embodiment, the weight ratio of the foregoing glycoside hydrolase to the foregoing Chrysanthemum morifolium may be about 1:1500-4000. In yet another embodiment, the weight ratio of the foregoing glycoside hydrolase to the foregoing Chrysanthemum morifolium may be about 1:750-2000. Furthermore, in another embodiment, the weight ratio of the foregoing glycoside hydrolase to the foregoing Chrysanthemum morifolium may be about 1:300-800.

Moreover, the temperature required for the aforementioned enzyme reaction may be about 25-45° C., such as 25° C., 30° C., 35° C., 36° C., 37° C., 37.5° C., 38° C., 39° C., 40° C., but it is not limited thereto. In one embodiment, the temperature of the aforementioned enzyme reaction may be about 37° C. In addition, the time required for the aforementioned enzyme reaction may be about 5-30 hours, such as 5-25 hours, 10-24 hours, but it is not limited thereto. In one embodiment, the time required for the aforementioned enzyme reaction may be about 16-24 hours.

Examples of the foregoing glycoside hydrolase may include, but are not limited to, glucosidase, galactosidase, glucuronidase, and any combinations thereof. The foregoing glucosidase may comprise α-glucosidase, β-glucosidase, or a combination thereof. The foregoing galactosidase may comprise α-galactosidase, β-galactosidase, or a combination thereof. Furthermore, the foregoing glucuronidase may comprise α-glucuronidase, β-glucuronidase, or a combination thereof.

In one embodiment, the foregoing at least one glycoside hydrolase may be glucosidase, and in this embodiment, the foregoing glucosidase is β-glucosidase. Moreover, in this embodiment, the weight ratio of the foregoing β-glucosidase to the foregoing Chrysanthemum morifolium may be about 1:200-10000, such as 1:3000-8000, 1:1500-4000, 1:750-2000; 1:300-800, but it is not limited thereto. In one embodiment, the weight ratio of the foregoing β-glucosidase to the foregoing Chrysanthemum morifolium may be about 1:3000-8000. In another embodiment, the weight ratio of the foregoing β-glucosidase to the foregoing Chrysanthemum morifolium may be about 1:1500-4000. In yet another embodiment, the weight ratio of the foregoing β-glucosidase to the foregoing Chrysanthemum morifolium may be about 1:1500. Moreover, in another embodiment, the weight ratio of the foregoing β-glucosidase to the foregoing Chrysanthemum morifolium may be about 1:750-2000. In yet another embodiment, the weight ratio of the foregoing β-glucosidase to the foregoing Chrysanthemum morifolium may be about 1:300-800.

In one embodiment, the foregoing at least one glycoside hydrolase may be glucosidase and glucuronidase. In this embodiment, the weight ratio of the glucosidase to the glucuronidase may be about 1:2-1:2, such as 1:1. 1.5:1, 2:1, 1:1.5, 1:2, etc., but it is not limited thereto. Moreover, in this embodiment, the weight ratio of the glucosidase and the glucuronidase to the foregoing Chrysanthemum morifolium may be about 1:200-10000, such as 1:3000-8000, 1:1500-4000, 1:750-2000, 1:300-800, but it is not limited thereto. In one embodiment, the weight ratio of the glucosidase and the glucuronidase to the foregoing Chrysanthemum morifolium may be about 1:1500-4000.

In addition, in the method for preparing an extract of Chrysanthemum morifolium with the effect of treating skin diseases of the present disclosure mentioned above, in one embodiment, water is used to perform the extraction procedure on the Chrysanthemum morifolium to obtain a water extract of Chrysanthemum morifolium.

Moreover, in this embodiment, the temperature of the extraction procedure mentioned above may be about 70-100° C., and time required for the extraction procedure mentioned above may be about 1-3 hours.

Furthermore, in the foregoing embodiment in which water is used as the extraction solvent, in one specific embodiment, in the step of adding at least one glycoside hydrolase to the extract solution to make an enzyme reaction occur to produce a precipitate, the at least one glycoside hydrolase which is used is glucosidase. This glucosidase may be β-glucosidase. Furthermore, the temperature of the foregoing enzyme reaction may be 25-45° C., such as 25° C., 30° C., 35° C., 36° C., 37° C., 37.5° C., 38° C., 39° C., 40° C., but it is not limited thereto, and in one specific embodiment, the temperature of the aforementioned enzyme reaction may be about 37° C. In addition, the time required for the foregoing enzyme reaction may be about 5-30 hours, such as 5-25 hours, 16-24 hours, but it is not limited thereto, and in one specific embodiment, the time required for the foregoing enzyme reaction may be about 16-24 hours. When the at least one glycoside hydrolase which is used is β-glucosidase, the weight ratio of the β-glucosidase to the *Chrysanthemum morifolium* may be about 1:300-10000, such as 1:3000-8000, 1:1500-4000, 1:750-2000, 1:400-800, but it is not limited thereto.

In addition, in the foregoing embodiment in which water is used as the extraction solvent, in another specific embodiment, in the step of adding at least one glycoside hydrolase to the extract solution to make an enzyme reaction occur to produce a precipitate, the at least one glycoside hydrolase which is used is glucosidase and glucuronidase. This glucosidase may be β-glucosidase while this glucuronidase may be β-glucuronidase. Furthermore, the temperature of the foregoing enzyme reaction may be 35-40° C., such as 35° C., 36° C., 37° C., 37.5° C., 38° C., 39° C., 40° C., but it is not limited thereto, and in one specific embodiment, the temperature of the aforementioned enzyme reaction may be about 37° C. In addition, the time required for the foregoing enzyme reaction may be about 5-30 hours, such as 5-25 hours, 16-24 hours, but it is not limited thereto, and in one specific embodiment, the time required for the foregoing enzyme reaction may be about 16-24 hours. When the at least one glycoside hydrolase which is used is β-glucosidase and β-glucuronidase, the weight ratio of the β-glucosidase and β-glucuronidase to the *Chrysanthemum morifolium* may be about 1:500-5000, such as 1:1500-4000, but it is not limited thereto. Furthermore, the weight ratio of the β-glucosidase to β-glucuronidase may be about 1:2-1:2, such as 1:1. 1.5:1, 2:1, 1:1.5, 1:2, etc.

With regard to the method for preparing an extract of *Chrysanthemum morifolium* with the effect of treating skin diseases of the present disclosure mentioned above, in another embodiment, in the step of adding at least one glycoside hydrolase to the extract solution to make an enzyme reaction occur to produce a precipitate, after the enzyme reaction, a cooling procedure may be further performed to promote production of the precipitate. The temperature of the cooling procedure may be about 2-15° C., such as 4° C., but it is not limited thereto. The time required for the cooling procedure may be about 2-24 hours, such as about 24 hours.

In another embodiment, the method for preparing an extract of *Chrysanthemum morifolium* with the effect of treating skin diseases of the present disclosure mentioned above may further comprise performing a washing procedure on the precipitate after the step of adding at least one glycoside hydrolase to the extract solution to make an enzyme reaction occur to produce a precipitate.

The aforementioned washing procedure may comprise the following steps, but it is not limited thereto.

First, the foregoing precipitate is re-dissolved with an alcohol solvent to form a mixture solution, and the mixture solution comprises a solution part and an insoluble matter. In one embodiment, examples of the alcohol solvent mentioned above may include, but are not limited to, methanol and ethanol. In one embodiment, the alcohol solvent mentioned above may be methanol.

After that, the solution part is concentrated and dried to obtain a washed precipitate. This precipitate has the effect of treating skin diseases.

By employing any method for preparing an extract of *Chrysanthemum morifolium* with the effect of treating skin diseases of the present disclosure mentioned above, after an extract of *Chrysanthemum morifolium* is subjected an enzyme treatment and that results in a bio-conversion, the active ingredients of the extract of *Chrysanthemum morifolium* can be raised, and the solubility of the ingredients of the extract of *Chrysanthemum morifolium* to the solvent can be changed to achieve the purpose of precipitation purification.

Furthermore, by using any method for preparing an extract of *Chrysanthemum morifolium* with the effect of treating skin diseases of the present disclosure mentioned above, the total content of two indicator ingredients of the extract of *Chrysanthemum morifolium*, luteolin and apigenin, can be greatly increased, and a high-purity extract of *Chrysanthemum morifolium* can be obtained only through a one-step enzyme treatment to obtain the effect of one-step purification. In the extract of *Chrysanthemum morifolium* obtained by any method for preparing an extract of *Chrysanthemum morifolium* with the effect of treating skin diseases of the present disclosure mentioned above, the sum of the contents of luteolin and apigenin may be 15-85 wt %, but it is not limited thereto.

The content ratio of the luteolin to the apigenin may be about 1:1-30, but it is not limited thereto. In one embodiment, the content ratio of the luteolin to the apigenin may be about 1:1-30, such as 1:1-25, but it is not limited thereto.

Accordingly, based on the foregoing, it can be known that the present disclosure also can provide an extract of *Chrysanthemum morifolium* with the effect of treating skin diseases, which can be obtained by any method for preparing an extract of *Chrysanthemum morifolium* with the effect of treating skin diseases of the present disclosure mentioned above.

The extract of *Chrysanthemum morifolium* obtained by the method for preparing an extract of *Chrysanthemum morifolium* with the effect of treating skin diseases of the present disclosure mentioned above may at least comprise, but is not limited to, two indicator ingredients, luteolin and apigenin. In the extract of *Chrysanthemum morifolium* mentioned above, the sum of the contents of luteolin and apigenin may be 15-85 wt %, but it is not limited thereto.

In the extract of *Chrysanthemum morifolium* obtained by the method for preparing an extract of *Chrysanthemum morifolium* with the effect of treating skin diseases of the present disclosure mentioned above, the content ratio of the luteolin to the apigenin may be about 1:1-30, but it is not limited thereto. In one embodiment, the content ratio of the luteolin to the apigenin may be about 1:1-30, such as 1:1-25, but it is not limited thereto.

Furthermore, the present disclosure may also provide another an extract of *Chrysanthemum morifolium* with the effect of treating skin diseases which may at least comprise, but is not limited to, two indicator ingredients, luteolin and apigenin while the content ratio of the luteolin to the apigenin may be about 1:1-30, but it is not limited thereto.

In one embodiment, the content ratio of the luteolin to the apigenin may be about 1:1-30, such as 1:1-25, but it is not limited thereto.

In addition, the present disclosure further provides a pharmaceutical composition for treating skin diseases. The pharmaceutical composition for treating skin diseases of the present disclosure may comprise, but is not limited to any aforementioned extract of *Chrysanthemum morifolium* with the effect of treating skin diseases of the present disclosure and a pharmaceutically acceptable vehicle, carrier or salt.

The pharmaceutically acceptable vehicles may act as a dilutent, dispersant or carrier for the active ingredient. The pharmaceutically acceptable vehicle may comprise materials commonly employed in skin care products such as water, liquid or solid emollients, silicone oils, emulsifiers, solvents, humectants, thickeners, powders, propellants and the like.

The vehicle may be formed from 80%-99.9 wt %, preferably from 90-99% by weight of the compositions mentioned above, and can, in the absence of other adjuncts, form the balance of the compositions.

Moreover, other specific ingredients which benefit skin, such as sunscreens, skin-lightening agents, and skin tanning agents may be also included in the compositions mentioned above. The vehicle may also further include adjuncts such as antioxidants, perfumes, opacifiers, preservatives, colourants and buffers.

In addition, in one embodiment, all of the compositions mentioned may be manufactured as a skin spreading form, including, but not limited to creams, ointments, gels, sprays, lotions, skin tonics, shampoos or mousses, etc. Skin sprays are generally composed of aerosolized copolymers, such as polyvinylpyrrolidone, vinyl acetate and the like, and may also function as a setting lotion. Skin gel preparations are similar to sprays in composition, but are in gel and alcohol free form, and can coat the skin. A skin mousse is foam released under pressure from an aerosolized can. Skin creams may be a hydrophobic or hydrophilic cream, ointment, gel, emollient, spray, lotion, skin tonic, shampoo or mousse, suitably with additional ingredients suitable for use in skin cream of types known in the art, and such further ingredients can include petrolatum, waxes, lanolin, silicone, liposomes, vegetable, mineral oils, plasticizers, fragrances, preservatives, a penetration enhancing agent, a pH adjusting agent or other suitable ingredients for skin creams. Such ingredients can moisturize skin, stabilize the active compound, increase the composition-skin contact to further raise local concentration and control the composition release.

The pharmaceutically acceptable carrier mentioned above may comprise, but is not limited to, a solvent, a dispersion medium, a coating, an antibacterial and antifungal agent, or an isotonic and absorption delaying agent, etc. which is suitable for pharmaceutical administration. The pharmaceutical composition can be formulated into dosage forms for different administration routes utilizing conventional methods.

Furthermore, the pharmaceutically acceptable salt mentioned above may include, but is not limited to, salts including inorganic cation, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also be organic salt, such as dicyclohexylamine salt, methyl-D-glucamine, and amino acid salt such as arginine, lysine, histidine, or glutamine.

The pharmaceutical composition of the present disclosure may be administered orally, parenterally by an inhalation spray, or via an implanted reservoir. The parenteral methods may comprise smearing affected regions, subcutaneous, intracutaneous, intravenous, intramuscular, intra-articular, intra-arterial, intrasynovial, intrasternal, intrathecal, and intraleaional injection, as well as infusion techniques.

An oral composition may include, but is not limited to, tablets, capsules, emulsions, and aqueous suspensions, dispersions and solutions.

Forms of topical compositions for smearing may comprise ointments, creams, solutions, gels, etc. but they are not limited thereto.

The pharmaceutical composition for treating skin diseases of the present disclosure may be a topical dosage form or a systemic dosage form, but it is not limited thereto. In one embodiment, the pharmaceutical composition for treating skin diseases of the present disclosure may be a topical dosage form, and examples of this topical dosage form may include, but are not limited to, ointments, creams, solutions, and gels.

Any foregoing pharmaceutical composition for treating skin diseases of the present disclosure can be used to treat various skin diseases, and has no specific limitation. Moreover, all of the foregoing pharmaceutical compositions for treating skin diseases of the present disclosure have excellent effects for treatment of various skin diseases, and they have excellent effects particularly for treating and/or alleviating skin inflammation.

In one embodiment, any foregoing pharmaceutical composition for treating skin diseases of the present disclosure can be used to treat allergic or contact dermatitis. In another embodiment, any foregoing pharmaceutical composition for treating skin diseases of the present disclosure can be used to treat autoimmune skin diseases, such as psoriasis.

EXAMPLES

Example 1

Preparation of Crude Extract PTB1

*Chrysanthemum morifolium* and 15 times its weight in water were mixed to form a mixture. The mixture was heated to ebullition (about 90-100° C.) to perform a heating extraction for 1 hour, and then solid residues therein were removed to obtain an extract solution. A vacuum concentrating and drying procedure was performed on the extract solution to obtain a crude extract PTB1. The ratio of the weight of the obtained crude extract PTB1 to the weight of the original herb material was about 1:1.5-4.

Example 2

Preparation of Enzyme-Treated Extract PTBX

*Chrysanthemum morifolium* and 15 times its weight in water were mixed to form a mixture. The mixture was heated to ebullition (about 90-100° C.) to perform a heating extraction for 1 hour, and then solid residues therein were removed to obtain an extract solution.

After the extract solution was cooled to room temperature, an enzyme, β-glucosidase, was added therein, and the ratio of the weight of the added enzyme to the weight of the original herb material was 1:1500. Next, the enzyme-containing extract solution was place in a 37° C. incubator to perform reaction for 16-24 hours. After the reaction was completed, the enzyme-reacted extract solution was placed in a 4° C. refrigerator for 24 hours to promote the production of precipitate.

Solid-liquid separation was performed on the solution to take the precipitate out and the precipitate was re-dissolved with methanol to from a mixture solution, and the mixture solution contained a solution part and an insoluble matter. After that, the solution part was taken out and a vacuum concentrating and drying procedure was performed thereon to obtain an enzyme-treated extract PTBX.

Example 3

1. Preparation of PTBX Ointment

A mixture of PTBX dry powder (1 g) and 95% ethanol (1.4 g), polyethylene glycol 400 (10 g), polyethylene glycol 4000 (4.5 g), ethoxylated hydrogenated castor oil (0.15 g) and high-purity deionized water (2.95 ml) was heated to 60° C. and stirred until it was uniformly mixed to make an external ointment dosage form, wherein 95% ethanol, polyethylene glycol 400, polyethylene glycol 4000, ethoxylated hydrogenated castor oil and high-purity deionized water were ingredients of vehicle.

2. Preparation of Simple Vehicle

A mixture of 95% ethanol (1.4 g), polyethylene glycol 400 (10 g), polyethylene glycol 4000 (4.5 g), ethoxylated hydrogenated castor oil (0.15 g) and high-purity deionized water (2.95 ml) was heated to 60° C. and stirred until it was uniformly mixed.

Example 4

Chemical Ingredients Change of the Extract of *Chrysanthemum morifolium* Before and after the Enzyme Treatment High-performance liquid chromatography (HPLC) was used to determine the content change of the indicator ingredients in the extract before and after the enzyme treatment.

In this experiment, two flavonoid ingredients, luteolin and apigenin, were selected as the indictor ingredients for the extract of *Chrysanthemum morifolium*, and the content changes of two sugar derivatives, luteolin 7-O-glucoside and apigenin-7-O-glucoside, respectively corresponding to the two indictor ingredients were also observed at the same time, and content analysis for each ingredient were performed by high-performance liquid chromatography.

High-performance liquid chromatography results for the extract of *Chrysanthemum morifolium* before and after the enzyme treatment are shown in Table 1.

According to Table 1, it is known that the total content of luteolin and apigenin of the extract of *Chrysanthemum morifolium* was raised from 0.063% (w/w, dry base), before the enzyme treatment, to 60.848% (w/w, dry base), after the enzyme treatment. In other words, the enzyme treatment used in the present disclosure is capable of greatly raising the total content of luteolin and apigenin and achieving the effect of one-step purification.

Example 5

Bio-Activity Change of the Extract of *Chrysanthemum morifolium* Before and after the Enzyme Treatment 1. Evaluation of In Vitro Keratinocyte Proliferation Inhibiting Activity of Enzyme-Treated Extract PTBX $5 \times 10^3$ HaCaT keratinocytes were inoculated into a 96 well plate, and placed in a 37° C. and 5% $CO_2$ incubator for culturing. After culturing for 16 hours, the cell numbers of this time point ($T_0$) was used as a reference point for cell proliferation, and the extract of *Chrysanthemum morifolium* from different processes, PTB1 or PTBX was added to the cells for co-culturing. After co-culturing for 48 hours ($T_{48}$), the supernatant in the plate was removed and 50 μl MTT solution (0.5 mg/mL) was added to the cells. After that, the plate was placed in a 37° C. and 5% $CO_2$ incubator for culturing 1.5 hours, and then 150 DMSO was added to the plate and the plate was shaken for 5 minutes. Then, absorbance at 570 nm was determined by a continuous wavelength microplate analyzer, and cell proliferation activity was calculated using the following formula:

Cell proliferation activity=$OD_{T0}/OD_{T48} \times 100$.

The experimental results are shown in Table 2.

2. Evaluation of In Vitro Inhibition on Inflammation Induced by Lipopolysaccharide (LPS) of Enzyme-Treated Extract PTBX $5 \times 10^5$ cells/mL of RAW264.7 cells were inoculated into a 96 well plate and cultured at 37° C. under 5% $CO_2$ overnight. The supernatant in the plate was removed and lipopolysaccharide (50 ng/mL) and different concentrations of PTB1 or PTBX were added to the cells.

After reacting for 24 hours, the supernatant in the plate was taken and NO content thereof was detected by Griess reagent (Promega, Cat. No. G2930).

Moreover, 50 μl of culturing medium containing MTT (0.5 mg/mL) was added to the cell part in the plate. After that, the plate was placed in a 37° C. and 5% $CO_2$ incubator for culturing 15-20 hours, and then 150 μL DMSO was added to the plate and the plate was shaken for 5-10 minutes.

TABLE 1

Ingredient content analysis for the extract of *Chrysanthemum morifolium* before and after the enzyme treatment

| Sample | Luteolin 7-O-glucoside (mg/g) | Apigenin-7-O-glucoside (mg/g) | Luteolin (mg/g) (Indicator ingredient) | Apigenin (mg/g) (Indicator ingredient) | Sum of luteolin and apigenin (mg/g) |
|---|---|---|---|---|---|
| PTB1 (Before the enzyme treatment) | 1.85 | 10.35 | 0.42 | 0.21 | 0.63 |
| PTBX (After the enzyme treatment) | 4.48 | 115.54 | 78.12 | 530.36 | 608.48 |

Finally, $OD_{570}$ was read by a continuous wavelength microplate analyzer, and cell viability was calculated using the following formula:

Cell viability (%)=(OD value of the experimental group/OD value of the control group)×100.

The experimental results are shown in Table 2.

3. Evaluation of In Vitro Inhibition Activity on Allergy Induced by DNFB of Enzyme-Treated Extract PTBX $2×10^4$ Normal Human Epidermal Keratinocytes (NHEKs) were inoculated into a 96 well plate, and then recombinant TNF-α (100 ng/ml; PeproTech Cat. No. 300-01A) was added to the plate for co-culturing with the cells. After co-culturing for 6 hours, DNFB (1 μM; Sigma Cat. No. D1529) and different concentrations of PTB1 or PTBX were added to the plate and the culturing was continued for 48 hours. After that, the supernatant in the plate was collected and Human IL-1β DuoSet ELISA (Invitrogen; Cat. No. BMS224) was used according to the manufacturer's recommended procedure to analyze the IL-1β content in the supernatant for determination of IL-1β expression level of the cells.

The experimental results are shown in Table 2.

4. Evaluation of In Vitro Inhibition Activity on Pruritus Caused by IL-31 of Enzyme-Treated Extract PTBX $2×10^4$ Normal Human Epidermal Keratinocytes (NHEKs) were inoculated into a 96 well plate, and then TLR1/2 stimulant, Pam3Cys-Ser-(Lys)4 (1 μg/ml; Abcam; Cat. No. ab14208) was added to the plate for co-culturing with the cells. After co-culturing for 6 hours, recombinant IL-31 (100 ng/ml; PeproTech; Cat. No. 200-31) and different concentrations of PTB1 or PTBX were added to the plate and the culturing was continued for 48 hours. After that, the supernatant in the plate was collected and Human CCL2/MCP-1 DuoSet ELISA (R&D; Cat. No. DY279) was used according to the manufacturer's recommended procedure to analyze the MCP-1 content in the supernatant for determination of MCP-1 expression level of the cells.

The experimental results are shown in Table 2.

Hairs of the back of Balb/c mice (6-8 week-old) were shaved, and the mice were divided into four groups which were the naïve group, the control group, the imiquimod (IMQ)+vehicle group and the experimental group, respectively. In the naïve group, no treatment is applied to the mice. In the control group, 50 mg imiquimod (IMQ) cream (Aldara; 3M Pharmaceuticals) was smeared on the backs of the mice, and the imiquimod cream was administered once time a day for 6 continuous days to induce parapsoriasis conditions on the mouse skin. In the imiquimod (IMQ)+vehicle group, 50 mg imiquimod cream (Aldara; 3M Pharmaceuticals) was smeared on the backs of the mice, and then the vehicle of ointment was topically smeared, and the imiquimod cream and the vehicle of ointment were administered once time a day for 6 continuous days. In the experimental group, 50 mg imiquimod cream (Aldara; 3M Pharmaceuticals) was smeared on the backs of mice, and then the PTBX ointment was topically smeared (50 mg), and the imiquimod cream and the PTBX ointment were administered once time a day for 6 continuous days.

After that, inflammation level of back skin of the mice was scored. Scoring item for the skin inflammation level comprises erythema and scaling. 0 score (no symptom) to 4 scores (serious) were assigned to back skin of the mice based on the severity of erythema and scaling, and the scores of erythema and scaling were summed up to calculate cumulative scores. The erythema score, scaling score and cumulative score of back skin of the mice of each group are shown in FIGS. 1A, 1B and 1C, respectively.

Before sacrificing, the psoriasis nidus of back skin of the mice were photographed and recorded, and after sacrificing, back skin of the mice was sliced, the epidermal thickness thereof was measured, and hematoxylin and eosin (H&E) stain was performed thereon. The photographs and H&E stain results for the back skin of the mice of each group and skin thickness of mice of each group are shown in FIGS. 1D and 1E, respectively.

TABLE 2

Analysis of in vitro bioactivity of the extract of *Chrysanthemum morifolium* before and after the enzyme treatment

| Sample | Total content of the four indicators (%) (Based on solid matter) | Keratoplasia $GI_{50}$ (μg/ml) | Inflammation induced by LPS $IC_{50}$ (μg/ml) | Allergy induced by DNFB $IC_{50}$ (μg/ml) | Pruritus caused by IL-31 $IC_{50}$ (μg/ml) |
|---|---|---|---|---|---|
| PTB1 (Before the enzyme treatment) | 1.28 | >100 | >100 | >50 | >10 |
| PTBX (After the enzyme treatment) | 72.8 | 25-50 | <25 | 1.3-2.5 | 0.6-1.3 |

According to Table 2, it is known that the effects of enzyme-treated extract PTBX on inhibiting keratinocyte proliferation, inflammation and contact allergy, and relieving itching are all significantly raised.

Example 6

Evaluation of Reducing Effects on Skin Inflammation of Parapsoriasis of Mice of Enzyme-Treated Extract PTBX In addition, detections of gene expression levels of keratin (K14) and filaggrin (FLG) were also performed on parts of tissue of the back skin of the mice, and the results are shown in FIGS. 1F and 1G.

FIGS. 1A-1E show that in the control group, administration of 50 mg imiquimod can result in erythema, scaling and increase of skin thickness of back skin of the mice, however, in the experimental group, by smearing 50 mg PTBX ointment, erythema and scaling of skin can be alleviated and skin thickness can be reduced.

For gene expression level, FIGS. 1F and 1G show that as compared to the naïve group, K14 expression of the control group significantly increases (###$p<0.001$), however, smearing 50 mg PTBX ointment has the effect of inhibiting K14 expression (*$p<0.05$). On the contrary, imiquimod results in decrease of FLG expression (#$p<0.05$) while smearing 50 mg PTBX ointment has a protection activity of maintaining FLG expression (**$p<0.01$). Experimental results are shown as Mean±Standard deviation.

Example 7

Investigation of Enzyme Treatment Process: Ratio of Enzyme to Extract

About 1 g dry powder of the crude extract PTB1 was re-dissolved with 50 ml sodium acetate buffer (pH 4.5), and then 0.1, 0.5, 1, 2 or 5 mg β-glucosidase was added therein, respectively. Next, the enzyme-containing solution was placed in a 37° C. incubator to perform the reaction for 16-24 hours. After the reaction was completed, the solution was placed in a 4° C. refrigerator for 24 hours to promote the production of precipitate.

Solid-liquid separation was performed on the solution to take the precipitate out and the precipitate was re-dissolved with methanol to from a mixture solution. After that, high-performance liquid chromatography was performed on the mixture solution, and the results are shown in Table 3.

TABLE 3

Investigation of ratio condition of enzyme to extract

| Amount of added enzyme | Ratio of weight of added enzyme to the weight of the original herb material (Ratio of the weight of the crude extract PTB1 to the weight of the original herb material is about 1:1.5-4) | Total content of the four ingredients (mg/g) |
| --- | --- | --- |
| 0.1 mg | 1:15000-40000 | ND |
| 0.5 mg | 1:3000-8000 | 346.26 |
| 1 mg | 1:1500-4000 | 327.85 |
| 2 mg | 1:750-2000 | 317.58 |
| 5 mg | 1:300-800 | 309.25 |

ND: Not detected

Based on the results shown in Table 3, it is known that, while 0.1 mg enzyme cannot produce precipitate, other amounts of enzyme all have the effect of producing precipitate.

Example 8

Investigation of Enzyme Treatment Process: A Variety of Enzyme

About 1 g dry powder of crude extract PTB1 was re-dissolved with 50 ml sodium acetate buffer (pH 4.5), and then 1 mg β-glucosidase, α-galactosidase or β-glucuronidase was added therein, respectively. The ratio of the weight of the added enzyme to the weight of the original herb material was about 1:1500-4000 (the ratio of the weight of the crude extract PTB1 to the weight of the original herb material was about 1:1.5-4). Next, the enzyme-containing solution was placed in a 37° C. incubator to perform the reaction for 16-24 hours. After the reaction was completed, the solution was placed in a 4° C. refrigerator for 24 hours to promote the production of precipitate.

The solution was centrifuged to isolate the precipitate and the precipitate was re-dissolved with methanol to from a mixture solution. After that, high-performance liquid chromatography was performed on the mixture solution to compare the indicator content difference before and after the enzyme treatment, and the results are shown in Table 4.

TABLE 4

Indicator content analysis for conversion results of different enzymes

| Sample | Luteolin 7-O-glucoside relative content (%) | Apigenin-7-O-glucoside relative content (%) | Luteolin relative content (%) | Apigenin relative content (%) |
| --- | --- | --- | --- | --- |
| PTB1 | 100 | 100 | 100 | 100 |
| PTB1 + β-glucosidase | 52.7 | 2.8 | 199.3 | 949.4 |
| PTB1 + α-galactosidase | 95.3 | 96.2 | 86.6 | 94.7 |
| PTB1 + β-glucuronidase | 76.9 | 99.5 | 163.8 | 145.0 |

According to the results of Table 4, it is known that both of β-glucosidase and β-glucuronidase are capable of increasing contents of luteolin and apigenin in the extract of *Chrysanthemum morifolium* through bio-conversion.

Example 9

Investigation of Enzyme Treatment Process: Combination of Enzymes

About 1 g dry powder of crude extract PTB1 was re-dissolved with 50 ml sodium acetate buffer (pH 4.5), and then 1 mg β-glucosidase and 1 mg α-galactosidase, or 1 mg β-glucosidase and 1 mg β-glucuronidase were added therein at the same time. The ratio of the weight of the added enzyme to the weight of the original herb material was about 1:750-2000 (the ratio of the weight of the crude extract PTB1 to the weight of the original herb material was about 1:1.5-4). Next, the enzyme-containing solution was placed in a 37° C. incubator to perform the reaction for 16-24 hours. After the reaction was completed, the solution was placed in a 4° C. refrigerator for 24 hours to promote the production of precipitate.

The solution was centrifuged to isolate the precipitate and the precipitate was re-dissolved with methanol to from a mixture solution. After that, high-performance liquid chromatography was performed on the mixture solution to compare the indicator content difference before and after the enzyme treatment, and the results are shown in Table 5.

TABLE 5

Indicator content analysis for conversion results of different enzymes

| Sample | Luteolin 7-O-glucoside relative content (%) | Apigenin-7-O-glucoside relative content (%) | Luteolin relative content (%) | Apigenin relative content (%) |
| --- | --- | --- | --- | --- |
| PTB1 | 100 | 100 | 100 | 100 |
| PTB1 + β-glucosidase + α-galactosidase | 35.5 | 2.0 | 194.9 | 897.7 |
| PTB1 + β-glucosidase + β-glucuronidase | 37.4 | 9.3 | 282.0 | 990.5 |

According to the results of Table 5, it is known that when β-glucosidase and β-glucuronidase are present at the same time, conversions of luteolin 7-O-glucoside and apigenin-7-O-glucoside to respective luteolin and apigenin can be raised.

Example 10

Investigation of Enzyme Treatment Process: Different Plants Belonging to *Chrysanthemum*

*Chrysanthemum indicum* L, *Chrysanthemum cinerariifolium* or *Chrysanthemum indicum* and 15 times its weight in water were mixed to form a mixture. The mixture is heated to ebullition (about 90-100° C.) to perform a heating extraction for 1 hour, and then solid residues therein were removed to obtain an extract solution.

After the extract solution was cooled to room temperature, an enzyme, β-glucosidase, was added therein, and the ratio of the weight of the added enzyme to the weight of the original herb material was about 1:1500. Next, the enzyme-containing extract solution was place in a 37° C. incubator to perform reaction for 16-24 hours. After the reaction was completed, the enzyme-reacted extract solution was placed in a 4° C. refrigerator for 24 hours to promote the production of precipitate.

After that, the extract solution was centrifuged and high-performance liquid chromatography was performed on the supernatant and the precipitate to determine whether other plants belonging to *Chrysanthemum* can also achieve the effects of precipitation through enzyme treatment or not, and an analysis of for in vitro keratinocyte proliferation inhibiting activity was performed on the precipitate, and the results are shown in Table 6.

TABLE 6

Activity analysis results of enzyme-conversion process for plants belonging to *Chrysanthemum*

| | Keratoplasia $GI_{50}$ (μg/ml) | Whether effects of precipitation purification occur? |
|---|---|---|
| *Chrysanthemum indicum* L | >200 | No |
| *Chrysanthemum indicum* L + β-glucosidase | >200 | No |
| *Chrysanthemum cinerariifolium* | 50-100 | No |
| *Chrysanthemum cinerariifolium* + β-glucosidase | 100-200 | No |
| *Chrysanthemum indicum* | >100 | No |
| *Chrysanthemum indicum* + β-glucosidase | >200 | No |

According to the results of Table 6, it is known that other plants belonging to *Chrysanthemum*, such as *Chrysanthemum indicum* L, *Chrysanthemum cinerariifolium* and *Chrysanthemum indicum*, all cannot be precipitated and purified through the enzyme treatment and keratinocyte proliferation inhibiting activity thereof cannot be raised through the enzyme treatment.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A method for preparing an extract of *Chrysanthemum morifolium* with an effect of treating skin diseases, comprising:
   (a) performing an extraction procedure on *Chrysanthemum morifolium* with an extraction solvent to obtain an extract solution; and
   (b) adding at least one glycoside hydrolase to the extract solution to make an enzyme reaction occur to produce a precipitate and increase the content of luteolin and the content of apigenin at the same time in the extract solution,
   wherein the precipitate is the extract of *Chrysanthemum morifolium* with an effect of treating skin diseases.

2. The method for preparing an extract of *Chrysanthemum morifolium* with an effect of treating skin diseases as claimed in claim 1, wherein the extract solution comprises water or alcohols.

3. The method for preparing an extract of *Chrysanthemum morifolium* with an effect of treating skin diseases as claimed in claim 1, wherein a temperature for the extraction procedure is about 70-100° C.

4. The method for preparing an extract of *Chrysanthemum morifolium* with an effect of treating skin diseases as claimed in claim 1, wherein time required for the extraction procedure is about 1-3 hours.

5. The method for preparing an extract of *Chrysanthemum morifolium* with an effect of treating skin diseases as claimed in claim 1, wherein the at least one glycoside hydrolases is at least one selected from a group consisting:
   glucosidase;
   galactosidase; and
   glucuronidase.

6. The method for preparing an extract of *Chrysanthemum morifolium* with an effect of treating skin diseases as claimed in claim 5, wherein the at least one glycoside hydrolases is glucosidase, and the glucosidase is β-glucosidase.

7. The method for preparing an extract of *Chrysanthemum morifolium* with an effect of treating skin diseases as claimed in claim 5, wherein the at least one glycoside hydrolases is glucosidase and glucuronidase, and the glucosidase is β-glucosidase and the glucuronidase is β-glucuronidase.

8. The method for preparing an extract of *Chrysanthemum morifolium* with an effect of treating skin diseases as claimed in claim 1, wherein the weight ratio of the at least one glycoside hydrolases to the *Chrysanthemum morifolium* is about 1:200-10000.

9. The method for preparing an extract of *Chrysanthemum morifolium* with an effect of treating skin diseases as claimed in claim 1, wherein temperature of the enzyme reaction is about 25-45° C.

10. The method for preparing an extract of *Chrysanthemum morifolium* with an effect of treating skin diseases as claimed in claim 1, wherein time required for the enzyme reaction is about 5-30 hours.

11. The method for preparing an extract of *Chrysanthemum morifolium* with an effect of treating skin diseases as claimed in claim 1, wherein the extract solution is water.

12. The method for preparing an extract of *Chrysanthemum morifolium* with an effect of treating skin diseases as claimed in claim 11, wherein temperature of the extraction procedure is about 70-100° C.

13. The method for preparing an extract of *Chrysanthemum morifolium* with an effect of treating skin diseases as claimed in claim 11, wherein the at least one glycoside hydrolases is β-glucosidase.

14. The method for preparing an extract of *Chrysanthemum morifolium* with an effect of treating skin diseases as claimed in claim 13, wherein the weight ratio of the β-glucosidase to the *Chrysanthemum morifolium* is about 1:200-10000.

15. The method for preparing an extract of *Chrysanthemum morifolium* with an effect of treating skin diseases as claimed in claim 11, wherein the at least one glycoside hydrolases is β-glucosidase and β-glucuronidase.

16. The method for preparing an extract of *Chrysanthemum morifolium* with an effect of treating skin diseases as claimed in claim 15, wherein a weight ratio of the β-glucosidase and the β-glucuronidase to the *Chrysanthemum morifolium* is about 1:200-10000.

17. The method for preparing an extract of *Chrysanthemum morifolium* with an effect of treating skin diseases as claimed in claim 15, wherein a weight ratio of the β-glucosidase to the β-glucuronidase is about 1:2-1:2.

18. The method for preparing an extract of *Chrysanthemum morifolium* with an effect of treating skin diseases as claimed in claim 1, wherein in step (b), after the enzyme reaction, a cooling procedure is further performed to promote production of the precipitate.

19. The method for preparing an extract of *Chrysanthemum morifolium* with an effect of treating skin diseases as claimed in claim 18, wherein the temperature of the cooling procedure is about 2-15° C., and time required for the cooling procedure is about 2-24 hours.

20. The method for preparing an extract of *Chrysanthemum morifolium* with an effect of treating skin diseases as claimed in claim 1, further comprising performing a washing procedure on the precipitate after step (b).

21. The method for preparing an extract of *Chrysanthemum morifolium* with an effect of treating skin diseases as claimed in claim 20, wherein the washing procedure comprises:
  (i) re-dissolving the precipitate with an alcohol solvent to form a mixture solution, wherein the mixture solution comprises a solution part and an insoluble matter; and
  (ii) performing a concentrating and drying process on the solution part to obtain a washed precipitate.

22. The method for preparing an extract of *Chrysanthemum morifolium* with an effect of treating skin diseases as claimed in claim 21, wherein the alcohol solvent comprises methanol or ethanol.

23. An extract of *Chrysanthemum morifolium* with an effect of treating skin diseases, which is obtained using the method for preparing an extract of *Chrysanthemum morifolium* with an effect of treating skin diseases as claimed in claim 1.

24. The extract of *Chrysanthemum morifolium* with an effect of treating skin diseases as claimed in claim 23, wherein the extract solution is water.

25. The extract of *Chrysanthemum morifolium* with an effect of treating skin diseases as claimed in claim 23, wherein the temperature of the extraction procedure is about 70-100° C.

26. The extract of *Chrysanthemum morifolium* with an effect of treating skin diseases as claimed in claim 23, wherein the time required for the extraction procedure is about 1-3 hours.

27. The extract of *Chrysanthemum morifolium* with an effect of treating skin diseases as claimed in claim 23, wherein the at least one glycoside hydrolases is β-glucosidase.

28. The extract of *Chrysanthemum morifolium* with an effect of treating skin diseases as claimed in claim 27, wherein the weight ratio of the *Chrysanthemum morifolium* to the β-glucosidase is about 1:200-10000.

29. The extract of *Chrysanthemum morifolium* with an effect of treating skin diseases as claimed in claim 23, wherein the at least one glycoside hydrolases is β-glucosidase and β-glucuronidase.

30. The extract of *Chrysanthemum morifolium* with an effect of treating skin diseases as claimed in claim 29, wherein a weight ratio of the β-glucosidase and β-glucuronidase to the *Chrysanthemum morifolium* is about 1:200-10000.

31. The extract of *Chrysanthemum morifolium* with an effect of treating skin diseases as claimed in claim 29, wherein a weight ratio of the β-glucosidase to β-glucuronidase is about 1:2-1:2.

32. An extract of *Chrysanthemum morifolium* with an effect of treating skin diseases, at least comprising the following two indicator ingredients:
  luteolin; and
  apigenin,
  wherein in the extract of *Chrysanthemum morifolium*, a content ratio of the luteolin to the apigenin is about 1:1-30.

33. The extract of *Chrysanthemum morifolium* with an effect of treating skin diseases as claimed in claim 32, wherein in the extract of *Chrysanthemum morifolium*, the content ratio of the luteolin to the apigenin is about 1:1-25.

34. A pharmaceutical composition for treating skin diseases, comprising:
  the extract of *Chrysanthemum morifolium* with an effect of treating skin diseases as claimed in claim 1; and
  a pharmaceutically acceptable vehicle, carrier or salt.

35. The pharmaceutical composition for treating skin diseases as claimed in claim 34, wherein the pharmaceutical composition is a topical dosage form, wherein the topical dosage form comprises an ointment, a cream, a solution or a gel.

36. The pharmaceutical composition for treating skin diseases as claimed in claim 34, wherein the skin diseases comprise treating allergic or contact dermatitis or psoriasis.

\* \* \* \* \*